United States Patent [19]

Copes et al.

[11] 3,988,351

[45] Oct. 26, 1976

[54] COMPLEXES OF POLYLACTAMS AND PHENOLIC COMPOUNDS

[75] Inventors: Joseph P. Copes, Easton, Pa.; David I. Randall, Leland, Mich.

[73] Assignee: GAF Corporation, New York, N.Y.

[22] Filed: Oct. 10, 1974

[21] Appl. No.: 513,873

Related U.S. Application Data

[63] Continuation-in-part of Ser. No. 193,974, Oct. 29, 1971, abandoned.

[52] U.S. Cl.......................... 260/326.25; 260/239 A; 260/239 R; 260/239.3 B; 260/239.3 R; 260/293.63; 260/293.64; 260/293.89; 424/346; 424/347; 424/244; 424/267; 424/274; 71/88; 71/94; 71/95; 21/58
[51] Int. Cl.².................................. C07D 207/26
[58] Field of Search............. 260/326.25, 239.3 R, 260/293.64, 293.89, 239 A, 239 R, 239.3 B; 424/346, 347; 71/118, 122; 21/58

[56] References Cited
UNITED STATES PATENTS

| | | |
|---|---|---|
| 2,578,526 | 12/1951 | Evans............................ 260/326.25 |
| 2,843,525 | 7/1958 | Robinson et al................ 424/346 X |
| 2,854,375 | 9/1958 | Shackell......................... 424/346 X |
| 3,157,641 | 11/1964 | Walles et al. .............. 260/326.25 X |
| 3,813,236 | 5/1974 | Allan ................................. 71/88 X |
| 3,824,190 | 4/1974 | Winicov et al.................. 424/346 X |

OTHER PUBLICATIONS

Schmulbach et al, "J. Organic Chem.," vol. 29, pp. 3122 & 3124 (1964).

Primary Examiner—Nicholas S. Rizzo
Assistant Examiner—Springer D. B.
Attorney, Agent, or Firm—Walter C. Kehm; Marilyn J. Maue

[57] ABSTRACT

A complex of a polylactam and a phenolic compound having the formula:

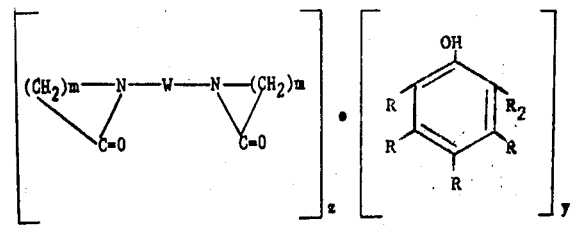

wherein $m$ is an integer from 2 to 5; $z$ and $y$ are expressed as a ratio of $z:y$ and is 1:1, 1:2, 2:3 or 1:4; W is alkylene having from 3 to 20 carbon atoms and each R and $R_2$ is hydrogen, halogen, hydroxyl, alkoxy of 1 to 4 carbon atoms, amido, alkyl hydroxy of from 1 to 4 carbon atoms, cyano or alkyl having from 1 to 12 carbon atoms, and wherein $R_2$ can also be alaninyl, or

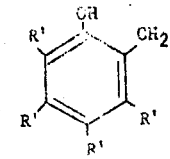

where each R' is hydrogen, hydroxyl, halo, cyano, alkyl having from 1 to 6 carbon atoms or nitro. The complexes are useful as germicides, insecticides, wood preservatives, plasticizers, and anti-oxidants.

22 Claims, No Drawings

COMPLEXES OF POLYLACTAMS AND PHENOLIC COMPOUNDS

This application is a continuation-in-part of application Ser. No. 193,974, filed Oct. 29, 1971, now abandoned, all commonly disclosed subject matter of which is incorporated herein by reference.

The complexes of the invention are useful as germicides, insecticides, wood preservatives, plasticizers, antioxidants and agents permitting the gradual release of various chemicals, primarily the phenol moiety. The gradual release of phenol in an insecticidal formulations for plants provides continuous activity over an extended period, such as, an entire growing season, without regard to conditions of humidity, drought or rain and without the need for additional applications during the growing season when applied in sufficient amount. In this regard the present compounds are particularly useful in the control of troublesome fungi which are known to over-winter and thus provide a constant source of plant infection.

The present invention relates to complexes of dilactams and phenolic compounds. In one aspect, it is concerned with comparatively low molecular weight, dilactam-phenolic complexes having a carbonyl infra-red band at 1650 cm$^{-1}$ representing a shift from 1680 cm$^{-1}$ for the dilactam and generally having a crystalline structure.

It has been postulated that mono-lactams and other amides form complexes with phenol; however, the prior art is totally lacking in any disclosure or teaching of definitely characterized chemical entities. Thus, for instance, Schmulbach et al, (J. Org. Chem. 29 3122-4, 1965) has reported studies including thermodynamic data based on the addition of phenol to a series of amide solutions including solutions of N-methylvalerolactam, epsilon-caprolactam, N,N-dimethylacetamide, N,N-dimethylpropionamide, N,N-dimethylformamide, N-methylcaprolactam and N-methylpyrrolidone. The studies were carried out in carbon tetrachloride; however, no actual compounds were isolated or characterized to establish that a complex, as opposed to a chemical mixture, was formed.

In accordance with the present invention, well defined, complexes of polylactams and phenolic compounds have now been prepared and investigated for useful applications so that they are not regarded as mere chemical curiosities.

The compounds of the present invention can be represented by the structural formula:

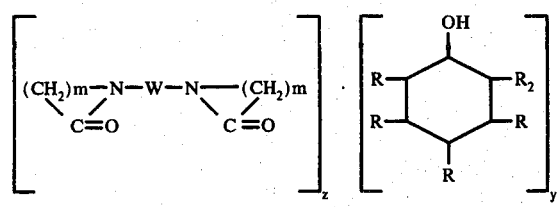

wherein $m$ is an integer from 2 to 5, preferably 3; $z$ is 1 and $y$ is an integer from 1 to 4, preferably 2 or 4; W is alkylene having 3 or more carbon atoms, preferably 3 to 10 carbon atoms and, each R and $R_2$ is hydrogen, halogen, hydroxyl, alkoxy of 1 to 4 carbon atoms, alkylhydroxy of 1 to 4 carbon atoms, cyano, amido, or alkyl having from 1 to 12 carbon atoms, preferably from 1 to 9 carbon atoms; and wherein $R_2$ can also be alaninyl, or

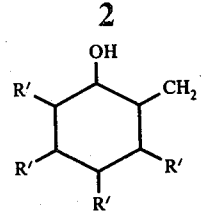

where R', hydrogen, hydroxyl, cyano, halo, nitro or alkyl having from 1 to 6 carbon atoms, preferably from 1 to 4 carbon atoms. Most preferred of the above complex compounds are those crystalline complexes wherein the phenolic moiety is phenol or a phenol substituted with a chlorine, bromine, hydroxyl, alkyl substituent or wherein $R_2$ is:

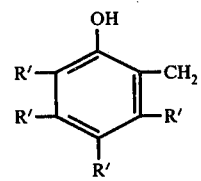

which is hydroxy benzyl or a chlorine or bromine mono- substituted hydroxy benzyl group.

The compounds of the foregoing structural formulae can generally be prepared by admixing the dilactam and the phenol or phenolic compound, warming the mixture until a homogeneous solution is formed and isolating the well defined resulting complex, which is crystalline for the dilactam complexes. In the present series of compounds prepared in accordance with the invention, a ratio of 2 phenolic hydroxyl groups for each pyrrolidone ring was established. Thus, in the case of reacting monohydroxylbenzene with hexamethylene bis (2-pyrrolidone), each of the two pyrrolidone rings complexed with two monohydroxybenzene molecules to provide a product having a molecular ratio of 1 lactam: 4 phenol. In the case of a difunctional hydroxy compound, such as dihydroxybenzene, each molecule of the dihydroxy compound complexed with one of the pyrrolidone rings in the dilactam to provide a product having a molecular ratio of 1 lactam: 2 dihydroxybenzene. Finally, in the case where a tetrahydroxybenzene is reacted with a dilactam, each pair of hydroxy groups reacts with each pyrrolidone ring to provide a product having a molecular ratio of 1 lactam: 1 tetrahydroxy benzene.

The dilactams of the present invention can be prepared by any one of several known methods including the reaction of $\alpha,\omega$-alkylenediamines with the desired $C_3$ to $C_6$ lactam, e.g. $\gamma$-butyrolactam, at 200° to 320° C. Also, the phenolic compounds employed in this invention can be prepared methods known in the art. In general, halogens are substituted on the phenol ring by reaction with hydrogen halide or halogen; or by partial fusion of a halobenzene (e.g. chlorobenzene) with alkali; and cyano groups are substituted by reaction of a halophenol with curprous cyanide or by the reaction of the phenol with cyanic acid. Polyhydroxy phenols are prepared by alkaline fusion of phenol sulfonic acids or polychlorobenzenes or by the hydrolysis of diazo phenol compounds. Numerous additional methods for preparing the compounds which form the present phenolic moieties are set forth in the art; however, the preparation of these phenolic compounds is not intended to form part of the invention as defined in the appended claims.

In carrying out the complexing reaction, it is usually advantageous to heat the mixture of the phenol and lactam in the presence or absence of a solvent until a clear homogeneous liquid is obtained, although preheating may not be necessary in every case where the complexing reaction is of an exothermic nature or where solvents are used. More specifically, the complexing reacting can be carried out at a temperature between about room temperature and up to about the boiling point of the complex; although a temperature in excess of 225° C is usually not required. However, in order to obtain a slower rate of reaction and more controlled distribution of the phenolic species with respect to the lactam, temperatures as low as about −10° C can be employed, if desired. The preferred temperature at which the reactants are mixed is within the range of from about room temperature and about 150° C. For the present reaction, there is no preferred order of addition of the reactants to the reaction zone, however, it has been found beneficial to agitate the mixture during the complexing reaction. Usually the reaction takes place in a relatively short period of time, i.e. from a few seconds to a few minutes, most often immediately upon contact after liquification of the reactive species. However, the contacting of reactants can be continued for a period of several hours to insure completion of the reaction. While it is preferred to conduct the reaction under atmospheric pressure, slightly subatmospheric or, in the case of relatively low boiling materials, slightly elevated pressures, from about 10 mm Hg to about 25 p.s.i.g., are also contemplated.

The dilactam and phenolic compounds are contacted in a mol ratio between about 5:1 and about 1:10, preferably between about 1:1 and 1:4 based on lactam ring: hydroxy group. Stoichiometric ratios are most preferred.

It is important that the mol ratio be maintained at least within the broad range since, with higher concentration of dilactam, an intractable solution is formed in which product crystallization does not take place and recovery of the product from the thickened solution practically possible. Conversely, the phenolic compound when employed in excess of 10:1 also causes difficulty in product recovery since separation of the normally solid hydroxy compound from the normally solid complex is extremely difficult. In view of these considerations, it is most preferred to maintain a mol ratio as close to 1:2 lactam ring to hydroxy group as is convenient. The dilactam and phenolic reactants of the present invention can be contacted in the presence or absence of a solvent. When both reactants are used in the form of solid particles, they can be mixed and heated to form a melt in the reaction zone. In cases where one of the reactants is a liquid, e.g. the dilactam species, the liquid reactant can be heated to a temperature above the melting point of the solid reactant and the solid added thereto. Still another method of contacting the reactive species includes mixing a solution of either one or both of the reactants. Specifically, the components of the reaction can be admixed by first forming a separate solution of each and gradually adding the solutions to the reactor or the components in the same solvent may be separately added to the reactor. Still another method comprises adding the components to a common liquid medium contained in a reactor. The concentration of each component in the solvent or dispersant is between about 1% by volume and up to the saturation limit of the liquid at the temperature employed. The more concentrated solutions are preferred. Suitable solvents for the dilactam and phenol species include water, chloroform, petroleum ether, benzene, toluene, hexane, heptane, acetic acid, cyclohexane, xylene, isooctane and others, i.e. inert neutral hydrocarbons and those used in the following Examples. If desired, a stabilizing agent may be added to the reaction mixture in a concentration of from 0.5 to 8% or higher; although stabilizers are usually not required. Suitable stabilizing agents are well known in the art and include hydrocarbon esters and 2,6-substituted hydrocarbon phenols.

After the complex is formed, which is usually marked by an exotherm or an exothermic rise in the temperature, the reactor is cooled, by allowing to cool gradually by rapid cooling or by flash chilling, generally to a temperature between about 40° and about 5° below the reaction temperature or the temperature at which the crystalline product is formed. The solvent is then removed by decantation and/or evaporation and the product is washed at a temperature between about 0° C and about 60° C with a suitable liquid such as hot water, or any of the above named solvents for the reactive species, and the wash liquid removed. The product is then recrystallized by warming with solvent until dissolved and then chilling. This procedure can be repeated as often as necessary to achieve the desired purity of the complex product. In some cases, when crystals are not formed with normal cooling, it may be desirable to cool the product liquid mixture to significantly lower temperatures, e.g. down to about −40° C, in order to initiate a crystalline state.

In regard to the reaction and subsequent separation and washing procedure, it is to be considered most surprising that the complexes are stable to hot solvents and in particular to hot water. In fact, many of the complexes formed in accordance with the invention could be crystallized out of water with no decomposition of the complex occurring.

Representative examples of suitable phenols for use in accordance with the invention include phenol, methyl phenol, butyl phenol, nonyl phenol, hydroquinone o, m- or p-cresol, 4-ethyl phenol, 3,4-dichlorophenol, 2,4,5-trichlorophenol 2,4,5-tribromophenol, hexabromophene, pentachlorophenol, o-, m- or p-bromophenol or fluorophenol, 3,4-dibromophenol, pyrogallol, phloroglucinol, catechol, 4-chloro-2,5-dimethylphenol, 2,6-dimethoxyphenol, 2'-hydroxychalcone, 4-methylcatechol, resorcinol, thymol, 4-butyl bisredamanol, 2,2'-methylenebis (2,4-dichlorophenol), L-Dopa, Dinex, bromoxynil, hexachlorophene, and including the phenols used in the examples.

Examples of suitable lactams for use in the present invention include N,N'-hexamethylenebis (2-pyrrolidone), N,N'-propylenebis (pyrrolidone), N,N'-trimethylenebis (2-pyrrolidone), N,N'-hexamethylenebis (3-propiolactam), N,N'-trimethylenebis (caprolactam), N,N'-decamethylenebis (2-pyrrolidone), N(3-pyrrolidonyl)-β-propiolactam, N,N'-octamethylenebis (lactam) and the like including the lactams employed in the examples.

The compounds in accordance with the invention have proved to be suitable for use as detoxified germicides. The phenols, although excellent germicides in themselves, are frequently irritating to the skin. The detoxification takes place in part due to the improved stability of the polylactam-phenolic complex which results in restricted release of the phenolic moiety and the reduced toxicity of the phenols in the complexed form. For these reasons, the present complexes have been found to be suitable for use as deodorants, antiseptic soaps, etc. It has also been found advantageous to use the complexes in accordance with the invention to avoid the result where such concentrations of chlorinated phenols are used that bodies of water are polluted thereby. Thus, the complexes of the hydroxyphenols and the lactams of the invention can be used to detoxify such phenols and are superior and important purification agents for drinking water from lakes and rivers.

Additionally, the complexes are suitable for use as plasticizers as well as antioxidants. The complexes result in reduced vapor pressure of the phenol involved, thus resulting in greater persistence in application and less odor and drifting of the medicament in connection with which they are used. It is also advantageous for the complexes of the invention to be used in the agricultural field in that they have been found to release agricultural chemicals, such as pentachlorophenol, at a controlled rate. Thus, the complexes in accordance with the invention may be used in admixture with fertilizers, soil sterilants, insecticides, larvicides, arachnidicides, nematocides, herbicides and the like, providing for release over greater periods and for prolonged effect with respect to retarded leaching of the active agent in connection with which they are used.

More specific illustrations of the usefulness of the compounds of the invention are the incorporation hereof into soaps, calamine lotion or into vaseline beeswax bases, vanishing cream or face creams, neutral oils, witch hazel, isopropanol, as anti-itching agents, as bacteriostats and as extreme pressure agents in slushing oils, hydraulic fluids and lube oils, as protective thermoplastic coatings for metals, as active agents in germicidal compositions, as stabilizers for edible fats, as anti-gas fading agents for dyed cellulose acetate fibers and films, as stabilizing agents for monomers, as rubber antioxidants, and the like.

For example, herbicidal compositions can be prepared from hexamethylenebis(2-pyrrolidone) and Bromoxynil.

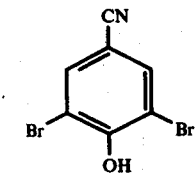

The complex is then dispersed as a liquid or dust and applied to the situs of various noxious weeds by methods and in concentrations disclosed in U.S. Pat. No. 3,397,054.

Insecticidal compositions can be prepared by reacting N,N'-methylbis(2-pyrrolidone) and 2',5-dichloro-4'-nitrosalicylanilide ethanolamine (mp. 216° C).

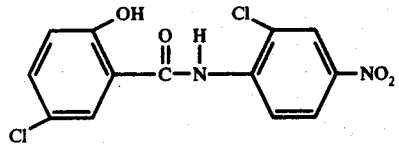

which in the form of a 2% Igepal (polyethroxylated hydrophobe manufactured by GAF) in water solution can be atomized and used as an insecticidal spray. A herbicidal composition of hexamethylenebis (2-pyrrolidone) and pentachlorophenol

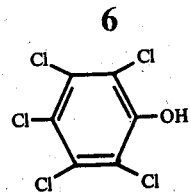

on incorporation into oil has proved useful as a wood preservation dip and weed killer spray.

The complex compounds of the invention are usualy employed in the above applications by dispersing the complex in a suitable inert solvent or carrier such as for example water, glycerol, heptane, olive oil, whole oil, soybean oil, petroleum or mineral oil, 100 SUS pale oil, butanol, propanol, isopropanol, hexachlorophene, acetone, methyl ethyl ketone, calamine lotion, Igepal, vaseline, beeswax base, benzene, toluene, xylene, cyclohexane, sawdust, atapulgite, kaoline, walnut shell flower, diatomaceous clay, fullers earth, talc, etc. or any of the solvents in the following examples or mixtures thereof and are employed therein in a concentration between about 0.005 and about 25% by volume, preferably between 0.01 and 1% by weight for skin applications and between 0.05 and 10% by weight for others depending on the particular field of application and the effective amount desired.

Generally, the present complex compounds are incorporated with a carrier or in a standard formulation by admixing therewith, preferably at a temperature between room temperature and about 130° C until a uniform mixture is obtained.

This invention will appear more fully from the examples which follow. These examples are set forth by way of illustration only, and it will be understood that the invention cannot be construed as limited in spirit or in scope by the details contained therein and that other species listed above can be substituted in the examples which follow to provide the corresponding dilactamphenolic complexes having similar chemical properties and uses. All values in the following examples are by weight unless otherwise indicated.

EXAMPLE 1

PREPARATION OF N,N'-HEXAMETHYLENEBIS(2-PYRROLIDONE) COMPLEX WITH PHENOL (1:4)

One mol hexamethylenebis(2-pyrrolidone) having a melting point of 25° C and 4 mols phenol having a melting point of 41° C were mixed together at 50° C. The generation of heat was noted and on cooling of the mixture, a crystalline mass was obtained. The crystals were recrystallized out of benzene and had a melting point of 48°–50° C. (Several crystallizations from benzene provides a product having a melting point of about 55°±1° C). Analysis of the crystals in this example established a 4.3% nitrogen content corresponding to a complex containing two phenol molecules for each pyrrolidone ring (2:1) or four phenol molecules for each hexamethylenebis pyrrolidone molecule (4:1 molar).

In the complex, the phenolic —OH group which was experimentally found to absorb in the infra-red at 3.0 microns, was found to absorb at 3.2 microns. The infra-red absorption of the pyrrolidone carbonyl usually observed at 6.0 in hexamethylenebis(2-pyrrolidone) was found at 6.32 microns. Although this complex possesses substantially good activity in all of the applications mentioned above it is particularly useful as a substantially odorless germicide for *Salmonella aureus*.

EXAMPLE 2

PREPARATION OF N,N'-(1,3-BUTYLENE)BIS-(2-PYRROLIDONE) COMPLEX WITH PHENOL (1:4 molar)

A complex was prepared by reacting 4 mols of phenol and 1 mol of N,N'-(1,3-butylene) bis-(2-pyrrolidone). The generation of heat was noted during the admixing of the lactam and phenol. Shifts were observed in the infra-red spectrum of the product indicating that a complex had been formed. In the infra-red spectrum the phenolic —OH was observed shifted from 3.0 to 3.17 microns and the pyrrolidone carbonyl was shifted from 6.0 to 6.12. The benzene hydrogens, observed at 13.35 and 14.57 microns respectively were shifted to 13.27 and 14.45 microns, respectively which indicate the formation of the complex. This complex displays substantially high activity for the applications mentioned above in Example 1.

EXAMPLE 3

PREPARATION OF N,N'-HEXAMETHYLENEBIS(2-PYRROLIDONE) COMPLEX WITH HYDROQUINONE (1:2 molar)

Hydroquinone 0.40 mol (44.0 g.) and N,N'-hexamethylenebis-(2-pyrrolidone) 0.20 mol (50 g.) were slurried together and a pronounced temperature rise of about 20° C was observed to take place after liquification. The slurry was heated to 160° C with stirring. On cooling, a crystalline mass was obtained. The crystals were recovered and recrystallized out of toluene-ethanol. The resultant crystalline complex melted at 133°–135° C. The complex could be readily crystallized from water and had a melting point of 133°–135° C.

The same compound was prepared from aqueous solution as follows: There were added to a solution of 0.88 g. hydroquinone in 30 cc water, 1.01 g. hexamethylenebis(2-pyrrolidone) in dropwise fashion. A crystalline precipitate appeared almost immediately.

Elemental analysis established that the complex was composed of 2 mols of hydroquinone and 1 mol hexamethylenebis pyrrolidone.

|   | Calculated | Found |
|---|---|---|
| C | 66.1 % | 66.12, 66.27% |
| H | 7.69% | 7.65% |
| N | 5.94% | 5.96% |

The compound was stable to boiling water. Although this complex is useful in all of the above-mentioned applications, it is particularly useful as a fungicide against powdery mildew, etc.

EXAMPLE 4

PREPARATION OF TRIMETHYLENEBIS(2-PYRROLIDONE) COMPLEX WITH (p-CRESOL) (1.4)

The procedure of Example 1 was generally followed except that the recovery was with hot water washing and the complex product was an oily liquid. Specifically, 0.016 mols (3.36 g) of N,N'-trimethylenebis(2-pyrrolidone) were stirred together with 6.78 g. (.064 mol) of p-cresol. Upon forming a homogeneous mixture, the temperature rose from about 25° to 35° C. The resultant complex was substantially insoluble in hot water but was soluble in hot toluene. This product is useful on wood having extended preservative life.

EXAMPLE 5

PREPARATION OF TRIMETHYLENEBIS(2-PYRROLIDONE) COMPLEX WITH NONYLPHENOL (1:4 molar)

In a reaction zone, 3.36 g. of trimethylenebis(2-pyrrolidone) (0.016 mol) and 14.08 g. nonylphenol (0.064 mol) were stirred together at a temperature of about 40° C. The complex was formed with about a 7° C rise in temperature. The complex remained stable in hot toluene and hot heptane.

Although this complex possesses reasonably good activity in the applications mentioned above, it is particularly useful as a skin emollient and is prepared as a composition by adding to water or alcohol to provide a solution containing between 0.001 and 0.1% by weight of the complex.

EXAMPLE 6

PREPARATION OF HEXAMETHYLENEBIS(2-PYRROLIDONE) COMPLEX WITH 3,4-DICHLOROPHENOL (1:4 molar)

In a reaction zone, 16.1 g. hexamethylenebis(2-pyrrolidone) and 41.7 g. 3,4-dichlorophenol were slurried together. A temperature rise of about 10° C was thereby noted. Following heating of the slurried mixture to 85° C, 60 cc of toluene were added and the resulting solution cooled to 0° C using an ice salt cooling bath. The crystalline mass thereby obtained was recrystallized from 40 cc toluene. The crystals were recovered, washed with petroleum ether, and dried to a weight of 35.3 g, melting point 54°–57° C.

Analysis showed a ratio of 4 molecules of 3,4-dichlorophenol to 1 molecule of hexamethylenebis pyrrolidone. Although this complex possesses substantially good activity in the applications mentioned above, it is particularly useful as a skin emollient and is prepared as a composition according to Example 5 above.

EXAMPLE 7

PREPARATION OF HEXAMETHYLENEBIS(2-PYRROLIDONE) COMPLEX WITH PYROGALLOL (1:2 molar)

A mixture of 20.16 g pyrogallol (0.04 mol) and 0.04 mol (10.1 g) hexamethylenebis-(2-pyrrolidone) was warmed to about 100° C whereupon the mixture formed a homogeneous liquid phase. The product on cooling yielded a brittle white solid having a melting point of 96° C. The following indications were observed by the infra-red analysis:

Band shifts in hexamethylenebis(2-pyrrolidone): the strong C—H stretching vibrations of hexamethylenebis2-pyrrolidone at 2920 $cm^{-1}$ are weak in the complex and appear at 2860 and 2924 $cm^{-1}$; strong C=O stretching vibrations at 1675 $cm^{-1}$ are shifted to 1650 $cm^{-1}$ in the complex; and hexamethylenebis (2-pyrrolidone) bands at 655, 570 and 512 $cm^{-1}$ do not appear in the complex.

Band shift in pyrogallol: The C=C in plane stretching vibrations at 1609 $cm^{-1}$ are shifted to 1619 in complex:

the C—O stretching and O—H in plane deformation at 1320 cm$^{-1}$ for pyrogallol are shifted to 1312 cm$^{-1}$ in the complex and the C—H out-of-plane deformation at 1768 cm$^{-1}$ is shifted to 1775 cm$^{-1}$ in complex.

This complex possesses substantially good activity in those applications mentioned above.

EXAMPLE 8

PREPARATION OF HEXAMETHYLENEBIS(2-PYRROLIDONE) COMPLEX WITH PHLOROGLUCINOL (1:2 molar)

A mixture of 20.16 g phloroglucinol (0.04 mol) and 0.04 mol (10.1 g.) hexamethylenebis(2-pyrrolidone) was heated to 107° C and then immediately cooled on a slab. Although the material did not crystallize well, the formation of the complex was established by the following shifts which were observed in the infra-red spectrum of the product as compared with the infra-red spectrum of the starting materials:

Band shifts in hexamethylenebis(2-pyrrolidone): the strong C—H stretching vibrations of hexamethylenebis(2-pyrrolidone) at 2840 to 2920 cm$^{-1}$ are weak in complex and appear at 2860 and 2925 cm$^{-1}$; strong C=O stretching vibrations of 1675 cm$^{-1}$ were shifted to 1615 cm$^{-1}$ in complex; in the complex, the 815 cm$^{-1}$ band split with an additional band introduced at 829 cm$^{-1}$; and hexamethylenebis(2-pyrrolidone) bands at 655 and 512 cm$^{-1}$ do not appear in complex.

Band shifts in pyrogallol: The C—O stretching and O—H in-plane deformation are shifted from 1155 cm$^{-1}$ to 1150 cm$^{-1}$ in complx and the C—H in-plane deformation in shifted from 1009 to 1000 cm$^{-1}$ in the complex.

Although this complex possesses substantially good activity in all of the applications mentioned above, it is particularly useful as a chemical reducing agent.

EXAMPLE 9

PREPARATION OF N,N'-HEXAMETHYLENEBIS(2-PYRROLIDONE) COMPLEX WITH 3,4-DICHLOROPHENOL (1:4)

Into an Erlenmeyer flask equipped with a stirrer were weighed 16.1 g. (0.064 mol) of N,N'-hexamethylenebis (2-pyrrolidone) and 41.7 g. (0.256 mol) of 3,4-dichlorphenol. An immediate temperature rise of 20° C was noted. The mixture then was heated to 85° C with liquefaction. The resultant product was cooled and then crystallized out of 60 cc of toluene and further crystallized out of 50 cc of toluene. Both crystallizations being carried out at 0° C. After washing with low boiling petroleum ether and air drying, there were recovered 35.5 g. of crystals which melted at 54°–57° C. (uncorrected).

|    | Calculated | Found |
|----|------------|-------|
| C  | 50.4       | 51.6  |
| H  | 4.47       | 4.75  |
| Cl | 31.3       | 30.81 |
| N  | 3.10       | 3.1   |

This complex possesses substantially good activity in all of the applications mentioned above.

EXAMPLE 10

PREPARATION OF HEXAMETHYLENEBIS(2-PYRROLIDONE) COMPLEX WITH 2,4,5-TRICHLOROPHENOL (1:4)

Into an Erlenmeyer flask equipped with a stirrer were weighed 4.0 g. (0.016 mol) of hexamethylenebis(2-pyrrolidone) and 12.7 g. (0.064 mol) 2,4,5-trichlorophenol. A 12° C rise in temperature was thereupon observed. The system was warmed until a homogeneous liquid was formed and then cooled to form a crystalline mass. After recrystallization from toluene-heptane, the melting point of the crystals was 82°–85° C. (uncorrected).

For $C_{38}H_{36}Cl_{12}N_2O_6$:

|    | Calculated | Found |
|----|------------|-------|
| C  | 43.7       | 43.7  |
| H  | 3.46       | 3.76  |
| Cl | 40.7       | 40.45 |
| N  | 2.69       | 2.64  |

This complex is substantially active for all applications mentioned above.

EXAMPLE 11

PREPARATION OF HEXAMETHYLENEBIS(2-PYRROLIDONE) COMPLEX WITH 2,2'-METHYLENEBIS(4,6-DICHLOROPHENOL) (1:2)

$$\left[\text{Hexamethyl-enebis-(2-Pyrrolidone)}\right] \cdot \left[\text{Cl}\begin{array}{c}\text{OH}\\\diagup\!\!\!\diagdown\end{array}\text{CH}_2\begin{array}{c}\text{OH}\\\diagup\!\!\!\diagdown\end{array}\text{Cl}\\\text{Cl}\quad\quad\quad\text{Cl}\right]_2$$

A slurry was prepared from 8.5 g. (0.025 mol) of 2,2'-methylenebis(4,6-dichlorophenol), and 3.2 g. (0.0125 mol) of hexamethylenebis(2-pyrrolidone). An exotherm of 10° was thereupon noted. The slurry was melted at a temperature of 135° C and then stirred for 10 minutes. On cooling, a hard, highly crystalline solid was obtained having a melting point of 88°–97° C. Crystallization out of heptane-toluene yielded a solid, melting at 95°–97° C.

Analysis for $C_{24}H_{40}Cl_8O_6$:

|    | Calculated | Found |
|----|------------|-------|
| C  | 51.6       | 51.5  |
| H  | 4.43       | 4.44  |
| N  | 3.11       | 3.05  |
| Cl | 30.6       | 30.0  |

This complex is substantially active for all applications mentioned above, and particularly, applications where controlled release of dichlorophenol is desired.

EXAMPLES 12 THROUGH 16

The following examples in Table I are provided to illustrate additional species of complex compounds within the scope of the present invention. In the following, the designated amounts of N,N-hexamethylenebis(2-pyrrolidone) and phenolic compound are gradually added to a glass reaction vessel with gentle stirring and heating until a homogeneous mixture is obtained. The vessel is maintained at a relatively low reaction temperature between about 20° and about 60° C and a rise in temperature marks the formation of the complex which is formed upon obtaining the melt. The formed crystalline mass is then dissolved in toluene while warming and subsequently cooled until the crystals appear. The toluene is then removed and the crystals dried for recovery of product.

such as *Pseudomonas aeruginosa* and *Bacillus subtilis* and is particularly useful against these as a bactericide of extended effective life. In contrast, when phenol is substituted for 2,4,6-trichlorophenol, this resulting product is more hygroscopic and thus more affected by changes in humidity.

A bacteriological evaluation was carried out as follows:

Two 0.1 ml. samples, one of hexamethylenebis(2-pyrrolidone) 2,4,6-trichlorophenol complex (in water at a concentration of 0.075 and 0.0075%); and two other samples of hexamethylenebis(2 pyrrolidone). phenol complex (in water at a concentration of 0.075 and 0.0075%), were placed on separate 0.5 inch diam- Table I

| Ex. No. | Mol of HMBP* | Mols/phenolic Compound | Reaction Temp. °C | Ratio of HMBP Phenolic in Complex | Character of Complex | Applications */% Conc. of complex in Carrier | | | | | | | | Range of Effective Con. of complex in Car. |
|---|---|---|---|---|---|---|---|---|---|---|---|---|---|---|
| | | | | | | G | I | H | W | P | A | C | R | S | |
| 12 | 1 | 2 of hexachlorophene | 166 | 1:2 | cryst. | 0.5 to 5 | | | | | | | | 0.1 to 1 | 0.1 to 5% |
| 13 | 1 | 4 of bayluscide⁺ | 220 | 1:4 | cryst. | | 2 to 5 | | 1 to 20 | | | | 0.5 to 10 | | 0.5 to 20% |
| 14 | 1 | 4 of perchlorophenol | 175 | 1:4 | cryst. | | 0.5 to 15 | 0.5 to 15 | 10 | | | | | | 0.5 to 15% |
| 15 | 1 | 4 of p-butyl redmanol | 70 | 1:4 | cryst. | | | | to 50 | | | | | 0.5 to 10 | 0.5 to 50% |
| 16 | 1 | 4 of 1,5-diisobutyl phenol | 110 | 1:4 | cryst. | | | | | | 0.5 to 10 | 0.5 to 10 | | | 0.5 to 10% |

*In the above table,
G = germicide;
I = insecticide;
H = herbicide;
W = wood preservative;
P = plasticizer;
A = antioxidant;
C = carrier for dyes;
R = plant growth regulant; and
S = skin emollient
⁻hexamethylenebis(2-pyrrolidone)
⁺2',5-dichloro-4'-nitro-salicylanilide

EXAMPLE 20

PREPARATION OF HEXAMETHYLENEBIS(2-PYRROLIDONE) COMPLEX WITH 2,4,6-TRICHLOROPHENOL (1:4)

Into an Erlenmeyer flask equipped with a stirrer were weighed 4.0 g. (0.016 mol) of hexamethylenebis pyrrolidone and 12.7 g. (0.064 mol) of 2,4,6-trichlorophenol (0.064 mol). Upon stirring a 10° C rise was observed. The system was warmed until a homogeneous liquid was formed and then cooled to form a crystalline mass. After recrystallization from toluene-heptane, the melting point of the crystals was 83° C. (uncorrected).

For $C_{38}H_{36}Cl_{12}N_2O_6$:

| | Calculated | Found |
|---|---|---|
| C | 43.7 | 43.7 |
| H | 3.46 | 3.76 |
| Cl | 40.7 | 40.45 |
| N | 2.69 | 2.64 |

The above complex possesses germicidal activity against Salmonella Aureus as well as other bacteria eter filter disks. The disks were then placed in contact with two separate but identical samples of active Salmonella aureus on agar plates. The samples were then incubated for 48 hours at 37° C.

Four control samples of 0.1, 0.01, 0.001 and 0.0001% phenol (in water) were also made up and placed on separate 0.5 inch diameter filter disks which were then contacted with 4 separate but identical samples of active Salmonella aureus on agar plates and incubated for 48 hours at 37° C. At the end of the incubation period, zones of inhibition around the disks were measured.

The results were as follows:

| Present Germicide | | % Concentraton | Zone o Inhibition (mm.) |
|---|---|---|---|
| HMBP . | 2,4,6-trichlorophenol | 0.075% | 8 |
| HMBP . | 2,4,6-trichlorophenol | 0.0075% | 2 |
| HMBP . | Phenol | 0.075% | trace |
| HMBP . | Phenol | 0.0075% | trace |
| Phenol | | 0.01% | 10 |
| Phenol | | 0.001% | 4 |
| Phenol | | 0.0001% | trace |

Although the phenol alone showed higher area of inhibition, the hexachlorophene complex has the advantage of being practically odorless, showing no hygroscopicity, or burning of the skin. It is believed that this product does not penetrate through the pores of human skin which makes it suitable for use as a skin emollient or in other applications where highly concentrated dosages of phenol causes burning of tissue, such as may occur in certain plants, such as certain ornamentals, succulents and legumes.

EXAMPLE 21

PREPARATION OF HEXAMETHYLENEBIS(2-PYRROLIDONE) COMPLEX WITH HEXACHLOROPHENE (1:2 mol)

Hexamethylenebis (2-pyrrolidone) 6.3 grams (0.025 mol) and hexachlorophene 20.6 grams (0.05 mol) were thoroughly mixed in a glass Kjeldahl flask and boiled for 24 hours. A solid precipitate (6.1 grams) was formed and separated by decanting the separated liquid. The complex of hexamethylenebis (2-pyrrolidone) . hexachlorophene (mp. 116°–117° C.) was obtained in 25% yield based on hexachlorophene. The ratio of hexamethylenebis(2-pyrrolidone) to hexachlorophene in the complex was 1:2.

The above complex is useful as bactericostat, and deodorant for use in soap and sprays, and particularly as an ingredient in surgical soaps. Tests have shown that 2 to 10% by weight concentration of this complex in soap can be applied to skin or as a disinfectant for medical instruments with the elimination of bacterial growth.

What we claim is:

1. A dilactam-phenolic complex having the formula:

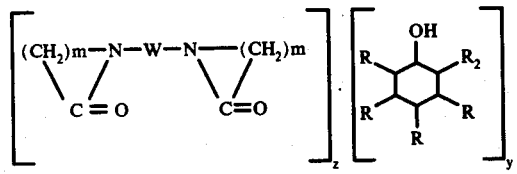

wherein $m$ is an integer from 2 to 5; $z$ is 1 or 2 and $y$ is an integer from 1 to 4; W is alkylene having from 3 to 20 carbon atoms, each R and $R_2$ is alkyl of from 1 to 12 carbon atoms, alkoxy of from 1 to 4 carbon atoms, amido, alkyl hydroxy of from 1 to 4 carbon atoms, cyano, hydrogen, halogen, or hydroxyl, and wherein $R_2$ can also be also be alaninyl or

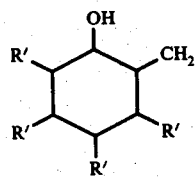

where each R' is hydrogen, hydroxyl, halo, cyano, alkyl of from 1 to 6 carbon atoms or nitro.

2. The dilactam-phenolic complex of claim 1 wherein the complex is crystalline.

3. A dilactam-phenolic complex of claim 1 wherein the ratio of $z:y$ is 1:1, 1:2 or 1:4 and W is alkylene of from 3 to 10 carbon atoms and each R and $R_2$ is alkyl of from 1 to 9 carbon atoms, methoxy, ethoxy, hydrogen, cyano, halogen, or hydroxy and wherein $R_2$ can also be alaninyl or hydroxy benzyl or a chlorine or bromine mono-substituted hydroxy benzyl radical.

4. A complex according to claim 1 designated hexamethylenebis(2-pyrrolidone). (phenol) in a ratio of 1:4.

5. A complex according to claim 1 designated N,N'-(1,3-butylene) bis(2-pyrrolidone). (phenol) in a ratio of 1:4.

6. A complex according to claim 1 designated N,N'-hexamethylenebis(2-pyrrolidone). (hydroquinone) in a ratio of 1:2.

7. A complex according to claim 1 designated N,N'-trimethylenebis(2-pyrrolidone). (p-cresol) in a ratio of 1:4.

8. A complex according to claim 1 designated trimethylenebis(2-pyrrolidone). (nonylphenol) in a ratio of 1:4.

9. A complex according to claim 1 designated hexamethylenebis (2-pyrrolidone). (3,4-dichlorophenol) in a ratio of 1:4.

10. A complex according to claim 1 designated hexamethylenebis(2-pyrrolidone). (pyrogallol) in a ratio of 1:2.

11. A complex according to claim 1 designated hexamethylenebis(2-pyrrolidone). Tetrachlororedmanol in a ratio of 1:2.

12. A complex according to claim 1 designated hexamethylenebis(2-pyrrolidone). (trichlorophenol) in a ratio of 1:4.

13. A complex according to claim 1 designated hexamethylenebis(2-pyrrolidone). Bromoxynil.

14. A complex according to claim 1 designated hexamethylenebis(2-pyrrolidone). pentachlorophenol.

15. A complex according to claim 1 designated hexamethylenebis(2-pyrrolidone). hexachlorophene.

16. A complex according to claim 1 designated hexamethylenebis(2-pyrrolidone). phloroglucinol.

17. The method of preparing the complex of claim 1 in which the dilactam is intimately mixed with the phenolic compound in a ratio of from 5:1 to 1:10 based on lactam ring to hydroxy group, at a temperature of from room temperature up to the boiling temperature of the corresponding complex compound under a pressure of from 10 mm. Hg. to about 25 psig. until an exothermic rise in temperature occurs and the reaction is substantially complete, cooling the reaction zone until a solid is formed from the reaction solution, recovering and washing the solid with an inert washing agent and drying to recover substantially pure product.

18. The method of claim 17 wherein the dilactam is contacted with the phenolic compound in a mol ratio between 1:1 and 5:1 based on each lactam ring of the dilactam for each lactam ring of the dilactam for each hydroxy group of the phenolic compound.

19. The method of claim 17 wherein the dilactam and phenolic compound are mixed and preheated to form a melt prior to raising the mixture to reaction temperature.

20. The method of claim 17 wherein at least one of the dilactam and phenolic compounds are dissolved in an inert solvent before introduction into the reaction zone.

21. The method of claim 18 wherein the inert solvent is selected from the group of water, benzene, methyl substituted benzenes, paraffinic hydrocarbons having from 6 to 10 carbon atoms, chlorinated $C_1$ to $C_6$ paraffins and mixtures thereof and the reactants are present in the reaction zone in a ratio of 1 mol of lactam to 10 mols of phenolic compound.

22. The method of claim 17 wherein the solid formed in the reaction zone is washed with an inert washing liquid selected from the group of petroleum ether, water, benzene, methyl substituted benzenes, paraffinic hydrocarbons having from 6 to 10 carbon atoms, chlorinated $C_1$ to $C_6$ paraffins and mixtures thereof.

* * * * *